(12) United States Patent
Kennedy et al.

(10) Patent No.: US 9,474,488 B2
(45) Date of Patent: Oct. 25, 2016

(54) NEUROTROPHIC ELECTRODE NEURAL INTERFACE EMPLOYING QUANTUM DOTS

(71) Applicants: Philip R. Kennedy, Duluth, GA (US); Steven A. Siebert, Atlanta, GA (US)

(72) Inventors: Philip R. Kennedy, Duluth, GA (US); Steven A. Siebert, Atlanta, GA (US)

(73) Assignee: Neural Signals, Inc., Duluth, GA (US)

( * ) Notice: Subject to any disclaimer, the term of this patent is extended or adjusted under 35 U.S.C. 154(b) by 483 days.

(21) Appl. No.: 14/217,949

(22) Filed: Mar. 18, 2014

(65) Prior Publication Data

US 2014/0200681 A1 Jul. 17, 2014

Related U.S. Application Data

(63) Continuation-in-part of application No. 12/042,742, filed on Mar. 5, 2008, now abandoned.

(60) Provisional application No. 60/893,161, filed on Mar. 6, 2007.

(51) Int. Cl.
*G01N 33/48* (2006.01)
*A61N 1/05* (2006.01)
*A61B 5/00* (2006.01)
*A61B 5/04* (2006.01)

(52) U.S. Cl.
CPC ............ *A61B 5/6864* (2013.01); *A61B 5/0006* (2013.01); *A61B 5/04001* (2013.01); *A61B 2562/0233* (2013.01); *A61B 2562/046* (2013.01)

(58) Field of Classification Search
None
See application file for complete search history.

*Primary Examiner* — Anna Skibinsky
(74) *Attorney, Agent, or Firm* — Bryan W. Bockhop; Bockhop Intellectual Property Law, LLC (57) ABSTRACT

A neural sensor includes a substrate defining an array of vias passing therethrough, a plurality of conductive surfaces, a light source, a plurality of groups of quantum dot-based luminescence units and a charge-coupled device (CCD) array. Each via allows a neurite to grow therethrough. Each conductive surface is adjacent to a different via and is electrically coupled thereto. The light source directs light toward the substrate. Each group of quantum dot-based luminescence units extends upwardly from a different one of the conductive surfaces generates light at a different predetermined wavelength when excited with light from the light source. Each luminescence unit changes its luminescence when electrically stimulated by a neural potential generated by a neurite. The CCD detects luminescence from each of the plurality of groups of quantum dot-based luminescence units and generates a signal representative of intensity of each wavelength of light detected.

19 Claims, 5 Drawing Sheets

NEUROTROPHIC ELECTRODE NEURAL INTERFACE EMPLOYING QUANTUM DOTS

CROSS-REFERENCE TO RELATED APPLICATION(S)

This application claims the benefit of U.S. Provisional Patent Application Ser. No. 60/893,161, filed Mar. 6, 2007, the entirety of which is hereby incorporated herein by reference.

This application is a continuation-in-part of, and claims the benefit of, U.S. patent application Ser. No. 12/042,742, filed Mar. 5, 2008, the entirety of which is hereby incorporated herein by reference.

BACKGROUND OF THE INVENTION

1. Field of the Invention

The present invention generally relates to a neural interface and, more specifically, to a transcutaneous neural interface.

2. Description of the Prior Art

Muscle paralysis affects over one hundred thousand people in the United States and approximately one million people worldwide. One class of patients who face severe difficulties in their daily lives is those with locked-in syndrome. Locked-in syndrome patients generally have a cognitively intact brain and a nearly completely paralyzed body. They are alert but cannot move or talk. They face a life-long challenge to communicate. Some patients may use eye movements, blinks or remnants of muscle movements to indicate binary signals, such as "yes" or "no." One approach used to provide assistance to patients with locked-in syndrome has been described in U.S. Pat. No. 4,852,573, which is hereby incorporated by reference (see, e.g., col. 5, ll. 39 et seq. for a discussion of use of nerve growth factor to enhance nerve growth into an electrode). In this approach, an electrode is implanted into the patient's brain and signals from the electrode may be used to control an electronic device.

Neural interfaces may be implanted in human subjects for communication and motor restoration applications. An ideal invasive neural interface would include multiple recording sites, isolation of each recording site to one axon to avoid cross-talk, mechanical stability, biocompatibility, long term recording capabilities, and a size minimization.

The ability to record neural activity over long durations is critically dependent upon proper neural interface design. Current approaches involve silicon microelectronic machining techniques for controllability and size reduction of passive electrodes. The desire for multiple recording sites has led to the development of multi-electrode arrays with corresponding high-density micro-ribbons. However these devices have not been able to achieve long term recording due to signal degradation and artifacts due to gliosis and micro-movements of the components.

One type of electrode recording system that has been available for long term human implantation is the neurotrophic electrode, which includes hollow glass cone containing gold recording wires that allow recording from axons grown into the glass cone under the influence of neural trophic factors. Recording from this reconstituted neuropil has produced action potentials (APs) that display robust signal-to-noise ratios over long time periods. The recording system uses transcutaneous FM transmission of the amplified system, thereby avoiding the need for wires. It is powered by air gap induction coils, obviating the need for batteries. This system has been implanted in six locked-in humans to provide them with control of a switch or a computer cursor, thus restoring synthetic speech, Internet access, environmental control, and other applications.

However, existing applications have implanted electrodes in only one or a few sites. This limited number of implanted sites limits the amount of information that can be transmitted to the external interface.

An increase in the number of electrode sites and size reduction of the recording area for individual axon isolation could substantially increase the likelihood of success in such applications as speech synthesis. The current neurotrophic electrode has a cone diameter of 20-25 µm and can contain anywhere between 10-50 individual neurites. Reducing the diameter into the 1-5 µm range would effectively limit the number of neurites grown into the device. The increase of neural data obtained from multiple recording sites would require additional wiring from the device to the amplifier system located outside of the skull. By applying a wireless method of transmitting signals from the neural interface to the electronics mounted on the skull, a high throughput of data can be achieved without the introduction of bulky micro-ribbons.

Direct optical imaging of neural activity has been demonstrated through voltage sensitive or Ca 2+-sensitive dyes with a charge coupled device (CCD) camera for detection. The CCD camera system allows simultaneously recording of multiple neural activities over a surface area at up to 5 kHz resolution. However, as the entire cortical surface area is bathed with the dye, there is no selectivity over the neurons being observed. The CCD camera is used to monitor electrical activity of all neurons over a 2-dimension visual field. This approach is not appropriate for long term recordings because of bleaching and phototoxic effects of the dyes.

Quantum dots have received substantial attention for biological marking applications utilizing photoluminescence, where higher energy light induces a characteristic (lower energy) quantum dot light emission. The electric dipole created at the quantum dot during optical light adsorption may be large enough to stimulate or inhibit neuronal firing. Quantum dots offer an advantage of increased efficiency. This is attributed to the inverse square relationship between charge and distance. By using either antibody-antigen recognition or peptide recognition groups, the quantum dots may be bound to the neuron and separated by less than 10 nanometers, as opposed to micron ranges in current neural interfaces.

The long term stability of such an approach has yet to be seen. Quantum dots (QDs) are mostly formed from Cd based heterostructures and although they are used routinely in vivo for marking applications, there are still existing questions as to their toxicity. Organic capping layers have been created to envelop the quantum dots, however these layers tend to act as electrical traps that increase efficiency for optical labeling applications, but reduce efficiency of opto-electrical conversion. In addition, quantum dots do not form long term interfaces, typically only lasting a matter of weeks. Tethered quantum dot films have been studied to address the question of stability but these films degraded within 3-5 days in primary neuron cultures. While cell binding techniques allow precise cell selection, they do not provide a method that can control interface construction at specified site areas.

Improvements to high density neural electrodes would substantially increase neural signal throughput and usability. Most notably, an increase in the number of electrode sites and size reduction of the recording area for individual axon isolation are critical requirements. Existing neurotrophic electrodes have a cone diameter of 20-25 μm and can contain anywhere between 10-50 individual neurites. Reducing the diameter into the 1-2 μm range would effectively limit the number of neurites grown into the device. The increase of neural data obtained from multiple recording sites using existing electrodes would require additional wiring from the device to the amplifier system located outside of the skull. By applying a wire-free method of transmitting signals from the neural interface to outside the skull, a high throughput of data can be achieved without the introduction of bulky cables.

Therefore, there is a need for a stable neural interface that transmits local neural action potentials from a plurality of recording sites.

SUMMARY OF THE INVENTION

The disadvantages of the prior art are overcome by the present invention which, in one aspect, is a device for interfacing neurons that includes a substrate that defines at least one via passing therethrough. The via is configured to allow at least one neurite to grow therethrough. A light generating unit is disposed adjacent to the substrate and is configured to generate light of a predetermined frequency when an action potential from the neurite is sensed. A light sensor that is spaced apart from the substrate is configured to assert a neural signal corresponding to the action potential when the light generating unit generates light of the predetermined frequency.

In another aspect, the invention is a neural interface for interfacing to a cerebral cortex of a patient in a region subtended by a portion of the patient's skull. The neural interface includes a neurotrophic electrode array. The neurotrophic electrode array includes a substrate, an amplifier and a plurality of quantum dots. The substrate defines a plurality of spaced-apart vias. Each via is treated with a neurotrophic factor that stimulates neurites to grow into the via when the neurotrophic electrode array is juxtaposed adjacent to the cerebral cortex. Each amplifier is adjacent to each via receives power from a thermoelectric generator and generates an amplified signal that corresponds to an action potential generated by a neurite that has grown into a corresponding via. The plurality of quantum dots are responsive to the amplified signal and emit a photonic signal in response to the amplified signal. A sensing and transmitting unit is spaced apart from the neurotrophic electrode array includes a charge-coupled device and a transmitter. The charge-coupled device senses light from each of the plurality of quantum dots and generates an electrical signal corresponding to the photonic signal. The transmitter is responsive to the electrical signal and generates a radio-frequency signal indicative of a state of the electrical signal.

In another aspect, the invention is a method of communicating an action potential to a receiving device, in which light of a predetermined frequency is emitted in response to an assertion of the action potential from a neurite. The light is sensed. Upon sensing the light, a wireless signal corresponding to the action potential is transmitted to the receiving device.

In another aspect, the invention is a neural sensor that includes a substrate, a plurality of conductive surfaces, a light source, a plurality of groups of quantum dot-based luminescence units and a charge-coupled device (CCD) array. The substrate defines an array of vias passing therethrough. Each via is configured to allow a neurite to grow therethrough. Each of the plurality of conductive surfaces is disposed on the substrate adjacent to a different one of the vias and is electrically coupled thereto. The light source is configured to direct light toward the substrate. Each group of quantum dot-based luminescence units extends upwardly from a different one of the plurality of conductive surfaces. Each group of quantum dot-based luminescence units is configured to luminesce so as to generate light at a different predetermined wavelength when excited with light from the light source. Each quantum dot-based luminescence unit is configured to change its luminescence at its predetermined wavelength when it is electrically stimulated by a neural potential generated by a neurite in contact with the conductive surface from which the quantum dot-based luminescence unit extends. The CCD array is configured to detect luminescence from each of the plurality of groups of quantum dot-based luminescence units and is configured to generate a signal representative of intensity of each wavelength of light that is detected.

In another aspect, the invention is a neural sensing device that includes a substrate, a plurality of conductive surfaces, a light emitting diode, a plurality of groups of quantum dot-based luminescence units, a CCD array and a skull replacement waveguide. The substrate defines an array of vias passing therethrough. Each via is configured to allow a neurite to grow therethrough. Each of the plurality of conductive surfaces is disposed on the substrate adjacent to a different one of the vias and electrically coupled thereto. The light emitting diode is configured to direct light toward the substrate. Each group of quantum dot-based luminescence units extends upwardly from a different one of the plurality of conductive surfaces. Each group of quantum dot-based luminescence units is configured to luminesce so as to generate light at a different predetermined wavelength when excited with light from the light source. Each quantum dot-based luminescence unit is configured to change its luminescence at its predetermined wavelength when it is electrically stimulated by a neural potential generated by a neurite in contact with the conductive surface from which the quantum dot-based luminescence unit extends. Each quantum dot-based luminescence unit includes: a conductive gold monolayer thin film affixed to one of the conductive surfaces; a chain molecule having a first end and an opposite second end, the first end coupled to the monolayer; and at least one quantum dot affixed to the second end of the chain molecule, the quantum dot configured to luminesce in response to illumination, wherein electrical stimulation of the conductive monolayer results in a geometric change of the chain molecule, thereby changing a luminescence parameter of light from the quantum dot. The CCD array is configured to detect luminescence from each of the plurality of groups of quantum dot-based luminescence units and is configured to generate a signal representative of which wavelengths of light are detected. The skull replacement waveguide is disposed so as to separate the plurality of groups of quantum dot-based luminescence units from the light source and the CCD array. The skull replacement waveguide is placed in a position to replace a missing portion of a user's skull. The skull replacement waveguide is configured to pass light from the light source to the quantum dot-based luminescence units.

In yet another aspect, the invention is a method of sensing neural potentials, in which a plurality of groups of quantum dot-based luminescence units is illuminated with light from a light source. Each group of quantum dot-based luminescence units is configured to luminesce so as to generate light at a different predetermined wavelength when excited with light from the light source. Each quantum dot-based luminescence unit is configured to change its luminescence at its predetermined wavelength when it is electrically stimulated by a neural potential generated by a neurite associated therewith. Each quantum dot-based luminescence unit includes: a conductive gold monolayer thin film affixed to one of the conductive surfaces; a chain molecule having a first end and an opposite second end, the first end coupled to the monolayer; and at least one quantum dot affixed to the second end of the chain molecule, the quantum dot configured to luminesce in response to illumination, wherein electrical stimulation of the conductive monolayer results in a geometric change of the chain molecule, thereby changing a luminescence parameter of light from the quantum dot. Changes light of each wavelength luminesced from the plurality of groups of quantum dot-based luminescence units is sensed, thereby determining which of the plurality of groups of quantum dot-based luminescence units have been excited by neural potentials.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

DETAILED DESCRIPTION OF THE INVENTION

A preferred embodiment of the invention is now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on."

Quantum dots possess a number of intrinsic and useful properties that are useful if integrated into neural interface devices. The emission wavelengths of quantum dots can be controlled by the size of the particles. Manufacturing of colloidal quantum dots is relatively simple and cost-effective compared to other optoelectronic devices. Embedding the quantum dots in polymers optimizes charge transport for electroluminescent devices.

Figure 1:
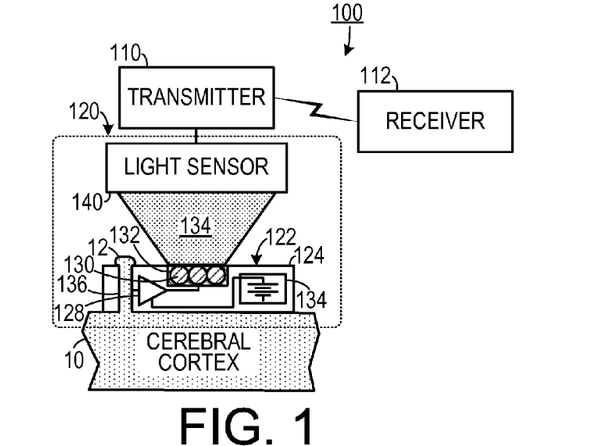
FIG. 1 is a schematic diagram of a quantum dot neural electrode sensing system.

As shown in FIG. 1, one exemplary embodiment of a neural interface 100 includes an action potential sensing system 120 that senses neural action potentials and generates a signal representative thereof. A transmitter 110 transmits the signal wirelessly to a remote receiver 112, which may then transmit the signal to a processor for use in such applications as device control and speech synthesis.

The action potential sensing system 120 includes a light generating unit 122 (or electrode) that is placed against a predetermined location of the patient's cortex 10 and that senses an action potential from a neurite 12 that extends from the cortex 10. The light generating unit 122 includes a substrate 124 that defines at least one via 136 (or hole) passing therethrough. An amplifier 128 senses action potentials asserted by the neurite 12 and generates an amplified signal corresponding to the action potentials. At least one quantum dot 130 (which may be enveloped in a polymer 132 to stabilize the quantum dot 130) generates light 134 of a predetermined frequency in response to the signal from the amplifier 128. The quantum dots 130 are excited by the electrical signal from the amplifier 128 and could include a fluorescent crystal of materials such as cadmium. A light sensor 140 that is spaced apart from the quantum dots 130 senses the light 134 and transmits a signal representative thereof to the transmitter 110. The neurite 12, having grown through the via 136 maintains the stability of the light generating unit 122 with respect to the cerebral cortex 10.

The amplifier 128 is powered by a power source 134, which in one embodiment includes a thermoelectric generator. The thermoelectric generator (such as a thermocouple) is a device that generates electricity in response to a temperature differential between the cerebral cortex 10 and the skin of the patient's head.

Figure 2:
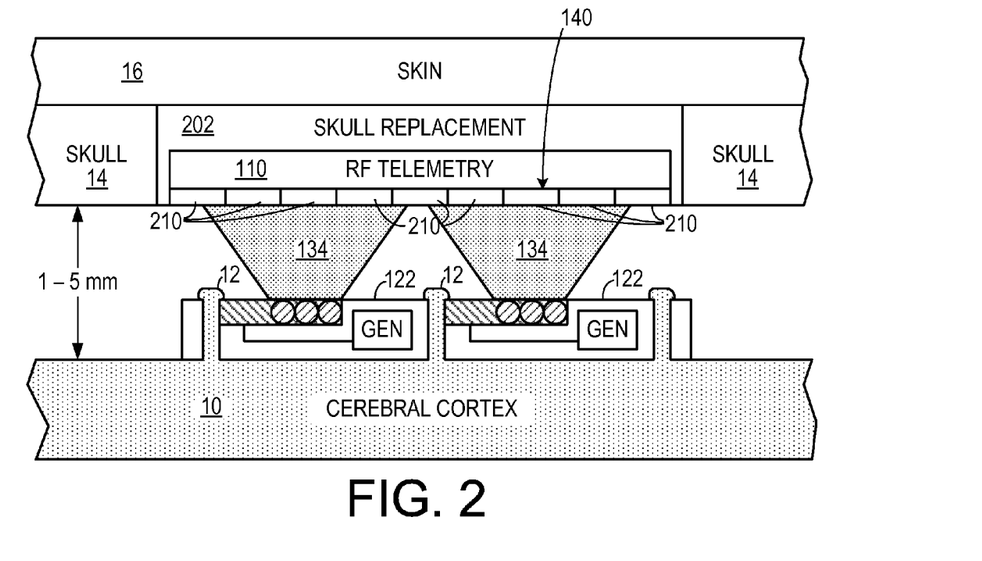
FIG. 2 is a schematic diagram of a quantum dot neural electrode array sensing system.

A portion of a simple quantum dot neural electrode array is shown in FIG. 2. Each neurite 12 has a different light generating unit 122 associated therewith. The light sensor 140 may include an array of charge coupled devices (CCD) 210 and may be placed with the transmitter 110 in a skull replacement component 202, which is placed in a hole in the patient's skull 14. The transmitter 110 may be powered in a manner similar to that of radio-frequency ID (RFID) tags, in which electromagnetic energy is transmitted to the device, which is then converted to electrical power. Once placed, the skin 16 may be sutured over the skull replacement component 202.

Figure 3:
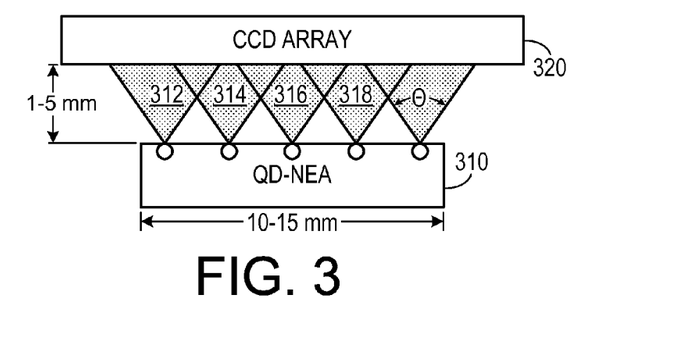
FIG. 3 is a schematic diagram of a frequency sensitive quantum dot neural electrode array sensing system.

In one embodiment, as shown in FIG. 3, a quantum dot neural electrode array 310 may include groups quantum dots that each generate light of a different frequency (312, 314, 316, 318, etc.) Each quantum dot group is placed so as to be exited by a different neurite. The CCD array 320 can sense the different frequencies. This allows precise differentiation of the action potentials generated by the different neurites. The light frequency of can be selected by selecting the size of the quantum dots being placed next to a via.

Figure 4:
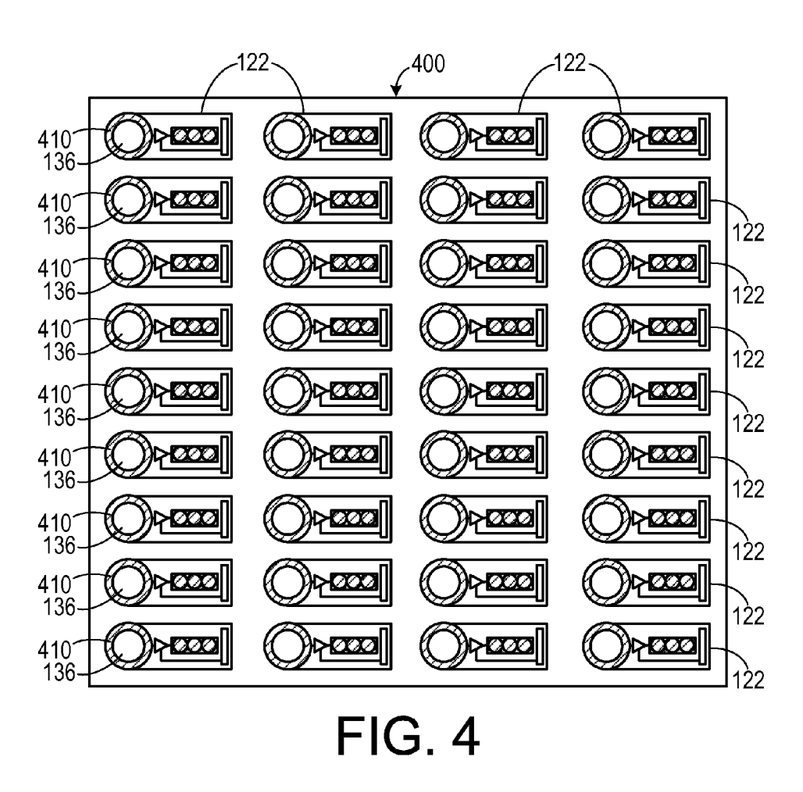
FIG. 4 is a top plan view of a quantum dot neural electrode array.

A top view of a quantum dot neural electrode array 400 is shown in FIG. 4. The array 400 includes a plurality of sensor members 122. In one embodiment, each via 136 may be treated with a neurotrophic factor 410 to promote the growth of neurites into the via 136.

The emission angle, $\Theta$, is determined in terms of efficiency. A quantum dot will emit light isotropically, that is in all directions. Only a small percentage of the emitted photons will be effective for CCD detection. Assuming the device will operate as a typical Lambertian emitter, a cosine function determines light intensity versus emission angle. The function is $N=N_o \cos \Theta$, where N is the radiant intensity, $N_o$ is the radiance normal to the emitting surface, and $\Theta$ is the emission angle. While the amount of detected light is effectively limited by the emission angle, this amount can be doubled by creating a reflective surface under the quantum dot light-emitting layer. If the signal intensity is limited to between 90-100% received at the CCD for useful data, $\Theta$ is then 25.9°. For separation distances between 1-3 mm, the range of areas of incident light onto the CCD array 320 from a quantum dot is determined to be between 0.209 mm² and 1.88 mm² respectively using trigonometric calculations.

The same calculations may be used to determine separation between the quantum dots. By spacing out the quantum dots on the array, local CCD sections are assigned to each QD. This makes signal processing simpler. Limiting the emission efficiency to 25% corresponds to quantum dot separation of 1.5-4.65 mm. A quantum dot neural electrode array with 10-15 mm diameter corresponds to areas of 78.5-177 mm². These ranges will allow an average of 31 quantum dot sets in the array for a 1-1.5 cm² device. This separation of the quantum dots also allows room for the MOSFET amplification and thermoelectric circuitry.

An advantage of the CCD approach is its ability for error correction. The implanted device will have vertical micro-movements associated with brain pulsations and general micro-movements transverse to the array. Whereas this would lead to a loss of signal in standard IR photodetectors and even low level RF signaling, in a large enough CCD array standard 2 dimensional signal processing will be able to track the movement of the quantum dot neural electrode array constantly. The CCD array can be constructed with this in mind; its area would be the area of the underlying QD-NEA plus additional area on the perimeter for the expected movement. A 4 cm² CCD array area could be sufficient. Vertical movement can be accounted for by assigning a few quantum dots to emit constantly a specific NIR frequency for continual monitoring and calibration.

Charge couple devices (CCD) are well known for low light detection applications, such as astronomical studies. The range of light detection ranges from UV to infrared and they are capable of single photon detection. The efficiency of photons converted to electrons can be determined from the dark current of the device. This is equivalent to electrical noise created in an environment without light. The light flux received and converted to an electrical current should be more than the dark current to be measured. Commercial CCD systems use 60 Hz for integration, but higher frequencies may be needed in monitoring neural activity. This is because the detection sampling of the CCD arrays should be made less than the time scale of the action potential. The Nyquist frequency, the lowest sampling frequency still able to accurately sample the waveform, would be 2 kHz to monitor action potential components up to 1 kHz, a time scale of 1 ms.

CCD arrays converted for neural recording operate at frequencies between 1-5 kHz which limits the effect of dark current; an integration time of 300 (3333 Hz) had a dark current noise of only 5 electrons. For a 2 kHz system this would correspond to 8 electrons. If the current is to be larger than the dark noise by a factor of 10, the minimum CCD current is then $2.56 \times 10^{-14}$ A (using $I=dq/dt$).

For a typical CCD element with quantum efficiency of 50%, 160 photons should be received at the detector every 0.5 ms for 2 kHz. It is recognized a large portion of the emitted light, approximately 97%, will be directed in directions away from the detector for an emission angle of 25.9°. This results in a transmission efficiency of 3%. The electroluminescence quantum efficiency is about 0.52%. This results in total system efficiency of 0.0078%, which results in a required current of $3.28^{-10}$ A to be generated at the quantum dots for successful transmission of neural signals. A thermoelectric generator supplying 1-5 V 1-10 µW, is able to supply a current from 200 nA to 1 µA. Considering the supply to operate MOSFET circuitry and quantum dots in parallel, the current then is equally split between each quantum dot for a total of 600 possible devices. This is more than ample power to operate the averaged array of 31 devices determined in the above calculations.

In one experimental embodiment the quantum dot—neurotrophic electrode array (QD-NEA) was approximately 20-50 µm thick and 1 cm in diameter. It was constructed from thinned, flexible silicon with polymer components. The inherent flexibility, durability, and minimum weight in this design were important, as the device is meant to be placed on the cortex surface. The vias were about 1-5 µm in diameter and the action potentials were measured and amplified with built in MOSFET circuitry.

The amplified signals were used to drive quantum dots to emit infrared light at specified frequencies assigned to each neuron. The intensity of the emitted light was directly related to the action potential voltage. The signals were then detected and sorted with a CCD array built into a skull replacement component.

The quantum dot neural electrode array structure disclosed herein is able to address these difficulties of specifying areas for interfacing and long term stability and toxicity control. In the quantum dot neural electrode array, the neurites are encouraged to grow into each electrode via, rather than having quantum dots applied directly to a cell body. The quantum dots are encapsulated in polymer packaging which is able to both protect them from the biological environment and confine any toxicity from escaping into the environment.

Figure 5A:
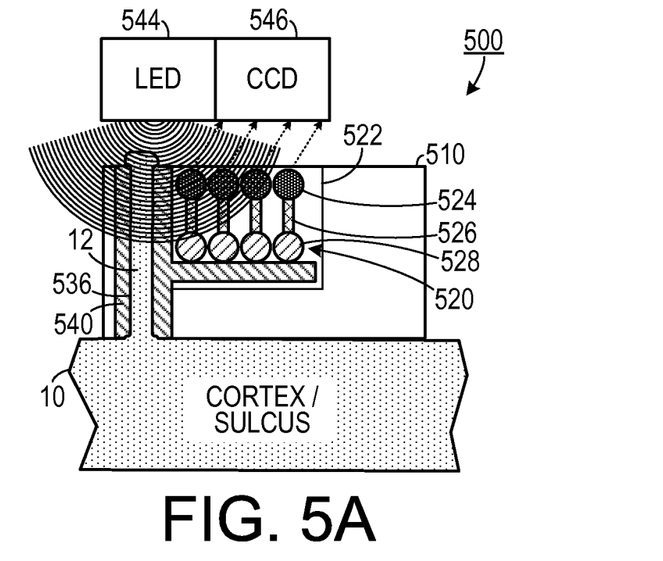
FIGS. 5A-5B are schematic diagrams demonstrating operation of an embodiment of a neural sensor.
Figure 5B:
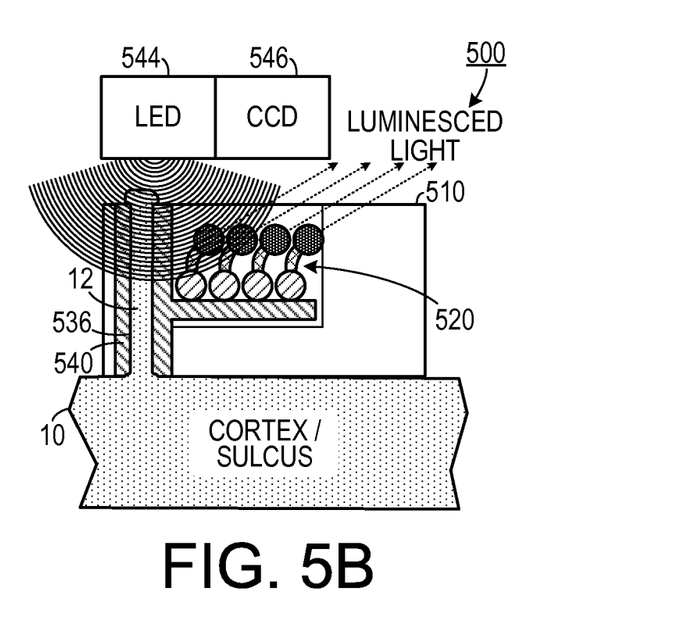
Figure 6:
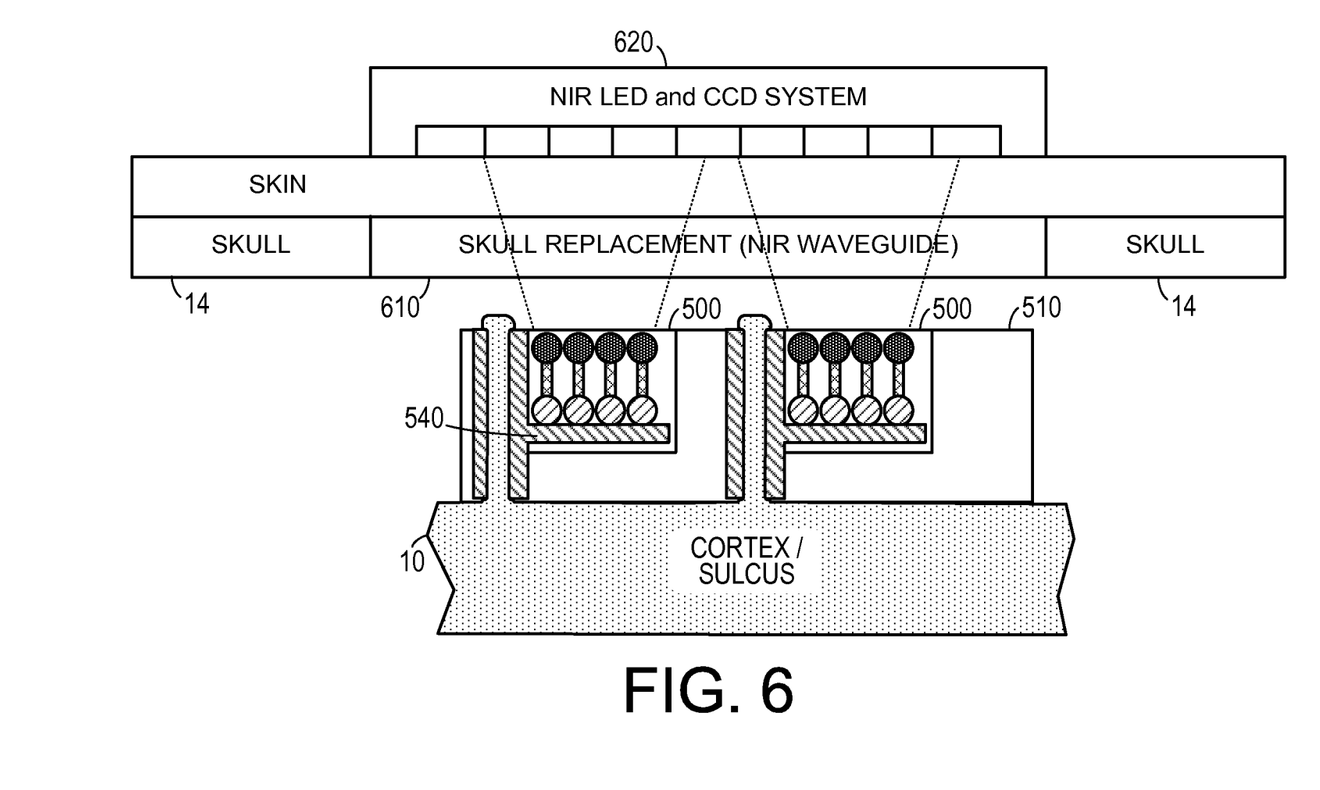
FIG. 6 is schematic diagram of a portion of a neural sensor array in use.
Figure 7:
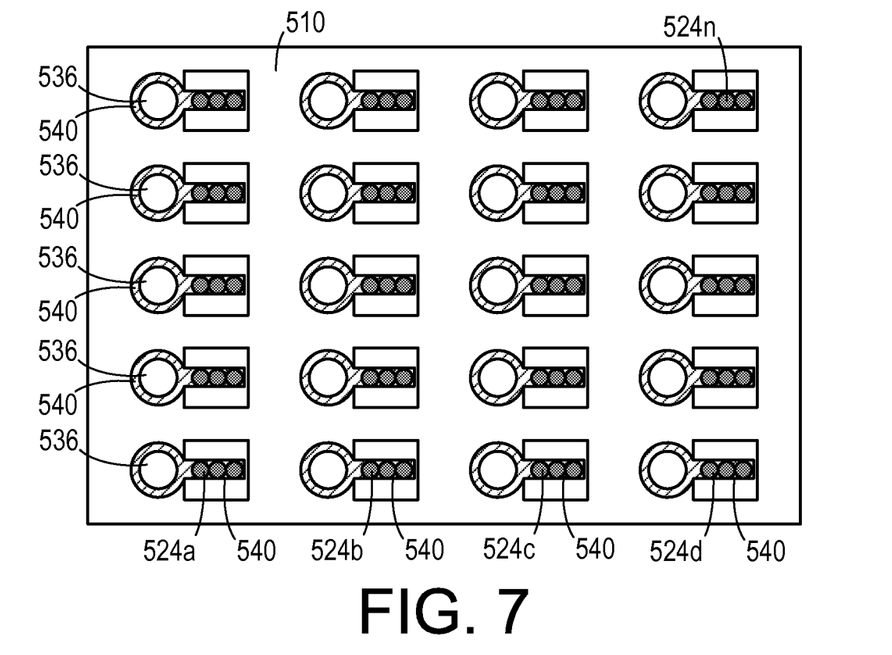
FIG. 7 is a plan view schematic diagram of a neural sensor array.

As shown in FIGS. 5A-5B, 6 and 7, one embodiment of a neural sensor 500 includes a substrate 510 (which could be made from a material such as a flexible silicon sheet or a polymer) that defines a plurality of vias 536 arranged in an array (as shown in FIG. 7) passing therethrough. The substrate is placed against a surface of a cortex 10 (such as a cerebral cortex or a cerebellar cortex), a sulcus or the like. Each via 536 may be treated with a neurotropic growth factor to encourage neurite growth therethrough. A conductive surface 540 is coupled to each via 536 so that when a neurite 12 has grown through the via 536, the neurite 12 will be electrically coupled to the conductive surface 540. A quantum dot-based luminescence unit 520 extends upwardly from a lateral portion of the conductive surface 540.

The quantum dot-based luminescence unit 520 includes conductive monolayer thin film 528 (such as a gold monolayer) affixed to one of the conductive surfaces. A chain molecule 526 (which could include a polyethylene glycol molecule, a DNA molecule, an RNA molecule, or the like) is coupled to the conductive monolayer thin film 528 and at least one quantum dot 524 is affixed to the chain molecule 526. The quantum dot 524 luminesces at a predetermined wavelength when illuminated. Different types of quantum dots luminesce at different wavelengths. Each group of quantum dots 524*a-n* in an array (as shown in FIG. 7) is chosen to luminesce at a different wavelength. The quantum dot-based luminescence unit 520 is packaged in a hermetically sealed micro-reservoir 522 that acts as a protective envelope.

The quantum dot 524 is illuminated by a light source 544, such as a light emitting diode (LED) and luminesces at its predetermined wavelength in response thereto. Luminescence from the quantum dot-based luminescence unit 520 is sensed by a light sensor 546, such as an array of charge coupled devices (CCDs), which is capable of detecting the intensities of different wavelengths being luminesced by different groups of quantum dots 524.

Assertion of a neural potential by the neurite 12 electrically stimulates the conductive monolayer 528 through the conductive surface 540. This causes a change in the chain molecule 526, which causes a change in a luminescence parameter of the quantum dot 524 that is detectable by the light sensor 546. (As shown in FIG. 5B, this may occur as a result of a geometric change in the chain molecule 526 in response to electrical stimulation. Such a change in geometry can result in quenching of the light luminesced due to it being redirected away from the light sensor 546.) Upon sensing light from an array of quantum dot-based luminescence units 520, the light sensor 546 generates a signal representative of which wavelengths of light are detected and their detected intensities.

As shown in FIG. 6, one way of employing a neural sensor 500 is to anchor it at a preselected location on the cortex or sulcus 10 and place a translucent skull replacement waveguide 510 in the hole defined by the skull 14 made for implants the sensor 500. The skull replacement waveguide 610 is made of a material that is transparent to the wavelength used to illuminate the sensor units 500 and the wavelengths being luminesced therefrom. (Typically, the wavelengths are near infra-red (NIR).) A combined LED and CCD light source/sensor system 620 is then placed outside of the skull replacement waveguide 610.

The neural sensor 500 can be fabricated in one method using standard microelectronic processes. The backside of the Si substrate 510 is metallized. A reservoir is created using photolithography and wet etching. Photoresist is used to pattern bottom electrode holes in the silicon and then holes (vias) are etched down to the metal layer. The photoresist s removed and gold will be electroplated up through the holes. Each gold pad will be able to bond gold nanoparticles and quantum dots on the top surface to form a voltage activated pixel. To avoid direct current flow between the quantum dots and gold electrodes, a thin dielectric layer is deposited and patterned with photolithography. Top gold electrodes are then patterned and deposited and the backside metal removed. Capacitive charges will be built up on the top gold electrodes once voltages are applied on the bottom gold electrode.

The above described embodiments, while including the preferred embodiment and the best mode of the invention known to the inventor at the time of filing, are given as illustrative examples only. It will be readily appreciated that many deviations may be made from the specific embodiments disclosed in this specification without departing from the spirit and scope of the invention. Accordingly, the scope of the invention is to be determined by the claims below rather than being limited to the specifically described embodiments above.

What is claimed is:

1. A neural sensor, comprising:
   (a) a substrate defining an array of vias passing therethrough, each via configured to allow a neurite to grow therethrough;
   (b) a plurality of conductive surfaces each disposed on the substrate adjacent to a different one of the vias and electrically coupled thereto;
   (c) a light source configured to direct light toward the substrate;
   (d) a plurality of groups of quantum dot-based luminescence units, each group of quantum dot-based luminescence units extending upwardly from a different one of the plurality of conductive surfaces and each group of quantum dot-based luminescence units configured to luminesce so as to generate light at a different predetermined wavelength when excited with light from the light source, each quantum dot-based luminescence unit configured to change its luminescence at its predetermined wavelength when it is electrically stimulated by a neural potential generated by a neurite in contact with the conductive surface from which the quantum dot-based luminescence unit extends; and
   (e) a CCD array configured to detect luminescence from each of the plurality of groups of quantum dot-based luminescence units and configured to generate a signal representative of intensity of each wavelength of light that is detected.

2. The neural sensor of claim 1, wherein the substrate comprises a material selected from a group consisting of: a flexible silicon sheet and a polymer sheet.

3. The neural sensor of claim 1, wherein the light source comprises a light emitting diode.

4. The neural sensor of claim 1, wherein each quantum dot-based luminescence unit comprises:
   (a) a conductive thin film;
   (b) a chain molecule having a first end and an opposite second end, the first end coupled to the monolayer; and
   (c) at least one quantum dot affixed to the second end of the chain molecule, the quantum dot configured to luminesce in response to illumination, wherein electrical stimulation of the conductive monolayer results in a geometric change of the chain molecule, thereby changing a luminescence parameter of light from the quantum dot.

5. The neural sensor of claim 4, wherein the conductive thin film comprises a gold monolayer.

6. The neural sensor of claim 4, wherein the chain molecule comprises a material selected from a group consisting of: polyethylene glycol, DNA and RNA.

7. The neural sensor of claim 1, further comprising a skull replacement waveguide, disposed between the plurality of groups of quantum dot-based luminescence units and the light source and placed in a position to replace a missing portion of a user's skull, the skull replacement waveguide configured to pass light from the light source to the quantum dot-based luminescence units.

8. The neural sensor of claim 1, further comprising a skull replacement waveguide, disposed between the plurality of groups of quantum dot-based luminescence units and the CCD array and placed in a position to replace a missing portion of a user's skull, the skull replacement waveguide configured to pass light from the quantum dot-based luminescence units to the CCD array.

9. The neural sensor of claim 1, wherein each of the plurality of groups of quantum dot-based luminescence units is hermetically sealed in a micro reservoir.

10. The neural sensor of claim 1, disposed on a surface of a selected one of: a cerebral cortex, a cerebellar cortex, a cortex and a sulcus.

11. A neural sensing device, comprising:
   (a) a substrate defining an array of vias passing therethrough, each via configured to allow a neurite to grow therethrough;
   (b) a plurality of conductive surfaces each disposed on the substrate adjacent to a different one of the vias and electrically coupled thereto;
   (c) a light emitting diode configured to direct light toward the substrate;
   (d) a plurality of groups of quantum dot-based luminescence units, each group of quantum dot-based luminescence units extending upwardly from a different one of the plurality of conductive surfaces and each group of quantum dot-based luminescence units configured to luminesce so as to generate light at a different predetermined wavelength when excited with light from the light source, each quantum dot-based luminescence unit configured to change its luminescence at its predetermined wavelength when it is electrically stimulated by a neural potential generated by a neurite in contact with the conductive surface from which the quantum dot-based luminescence unit extends, each quantum dot-based luminescence unit comprising:
(i) a conductive gold monolayer thin film affixed to one of a plurality of conductive surfaces surfaces;
(ii) a chain molecule having a first end and an opposite second end, the first end coupled to the monolayer; and
(iii) at least one quantum dot affixed to the second end of the chain molecule, the quantum dot configured to luminesce in response to illumination, wherein electrical stimulation of the conductive monolayer results in a geometric change of the chain molecule, thereby changing a luminescence parameter of light from the quantum dot;
(e) a CCD array configured to detect luminescence from each of the plurality of groups of quantum dot-based luminescence units and configured to generate a signal representative of which wavelengths of light are detected; and
(f) a skull replacement waveguide, disposed so as to separate the plurality of groups of quantum dot-based luminescence units from the light source and the CCD array, the skull replacement waveguide placed in a position to replace a missing portion of a user's skull, the skull replacement waveguide configured to pass light from the light source to the quantum dot-based luminescence units.

12. The neural sensing device of claim 11, wherein the substrate comprises a material selected from a list consisting of: a flexible silicon sheet and a polymer sheet.

13. The neural sensing device of claim 11, wherein the chain molecule comprises a material selected from a group consisting of: polyethylene glycol, DNA and RNA.

14. The neural sensing device of claim 11, wherein each of the plurality of groups of quantum dot-based luminescence units is hermetically sealed in a micro reservoir.

15. The neural sensing device of claim 11, disposed on a surface of a selected one of: a cerebral cortex, a cerebellar cortex, a cortex and a sulcus.

16. A method of sensing neural potentials, comprising the steps of:
(a) illuminating a plurality of groups of quantum dot-based luminescence units with light from a light source, each group of quantum dot-based luminescence units configured to luminesce thereby generating light at a different predetermined wavelength when excited with light from the light source, each quantum dot-based luminescence unit configured to change its luminescence at its predetermined wavelength when it is electrically stimulated by a neural potential generated by a neurite associated therewith, each quantum dot-based luminescence unit comprising:
(i) a conductive gold monolayer thin film affixed to one of a plurality of conductive surfaces surfaces;
(ii) a chain molecule having a first end and an opposite second end, the first end coupled to the monolayer; and
(iii) at least one quantum dot affixed to the second end of the chain molecule, the quantum dot configured to luminesce in response to illumination, wherein by a neural potential generated by a neurite, of the conductive monolayer results in a geometric change of the chain molecule, thereby changing a luminescence parameter of light from the quantum dot;
(b) sensing changes light of each wavelength luminesced from the plurality of groups of quantum dot-based luminescence units, thereby determining which of the plurality of groups of quantum dot-based luminescence units have been excited by neural potentials.

17. The method of claim 16, further comprising the step of passing the light from the light source through a skull replacement waveguide coupled to a skull.

18. The method of claim 16, wherein the chain molecule comprises a material selected from a group consisting of: polyethylene glycol, DNA and RNA.

19. The method of claim 16, further comprising the step of passing the light luminesced from the quantum dot-based luminescence units through a skull replacement waveguide coupled to a skull.

* * * * *